US005654488A

United States Patent [19]
Krause et al.

[11] Patent Number: 5,654,488
[45] Date of Patent: Aug. 5, 1997

[54] PREPARATION OF ASTAXANTHIN

[75] Inventors: Wolfgang Krause, Brühl; Klaus Henrich, Hassloch; Joachim Paust, Neuhofen; Hansgeorg Ernst, Speyer, all of Germany

[73] Assignee: BASF Aktiengesellschaft, Ludwigshafen, Germany

[21] Appl. No.: 616,459

[22] Filed: Mar. 15, 1996

[30] Foreign Application Priority Data

Mar. 18, 1995 [DE] Germany .................. 195 09 955.9

[51] Int. Cl.⁶ .................................................. C07C 45/00
[52] U.S. Cl. ........................ 568/345; 568/343; 568/352
[58] Field of Search ........................ 568/345, 343, 568/352

[56] References Cited

U.S. PATENT DOCUMENTS

| 3,078,256 | 2/1963 | Wittig et al. | 260/666 |
| 3,989,758 | 11/1976 | Rüegg et al. | 260/602 |
| 4,156,090 | 5/1979 | Kienzle | 560/61 |
| 4,952,716 | 8/1990 | LuKac et al. | 556/482 |
| 5,210,314 | 5/1993 | Ernst et al. | 568/345 |
| 5,455,362 | 10/1995 | Ernst et al. | 549/437 |

FOREIGN PATENT DOCUMENTS

| 0 005 748 B1 | 12/1979 | European Pat. Off. . |
| 0 005 749 B1 | 12/1979 | European Pat. Off. . |
| 0 101 597 B1 | 2/1984 | European Pat. Off. . |
| 0 283 979 | 9/1988 | European Pat. Off. . |
| 0 329 754 B1 | 8/1989 | European Pat. Off. . |
| 0 440 037 A1 | 8/1991 | European Pat. Off. . |
| 1 163 369 | 4/1958 | France . |
| 1 383 944 | 11/1964 | France . |
| 954 247 | 12/1956 | Germany . |
| 1 068 703 | 4/1960 | Germany . |
| 26 53 838 | 6/1977 | Germany . |

OTHER PUBLICATIONS

Helv. Chim. Acta 64 (1981) pp. 2405–2418, 2436–2446, 2447–2462.
"Carotenoids", O. Ister, Birkhäuser–Verlag (1971), pp. 140–141.

Primary Examiner—Joseph McKane
Attorney, Agent, or Firm—Oblon, Spivak, McClelland, Maier & Neustadt, P.C.

[57] ABSTRACT

Improved process for the preparation of astaxanthin by Wittig reaction of 2 mol of 3-methyl-5-(2,6,6-trimethyl-3-oxo-4-hydroxy-1-cyclohexenyl)-2,4-pentadienyltriarylphosphonium salts with one mol of 2,7-dimethyl-2,4,6-octatrienedial avoiding the use of halohydrocarbons as solvents.

5 Claims, No Drawings

PREPARATION OF ASTAXANTHIN

The invention relates to an improved process for preparing the $C_{40}$-carotenoid astaxanthin by a double Wittig reaction of a 3-methyl-5-(2,6,6-trimethyl-3-oxo-4-hydroxy-1-cyclohexenyl)-2,4-pentadienyltriphenylphosphonium salt (asta-$C_{15}$-triphenylphosphonium salt) with 2,7-dimethyl-2,4,6-octatrienedial ($C_{10}$-dial).

Astaxanthin is a natural pigment which is in great demand for coloring foodstuffs, salmon and trout. Accordingly, a large number of methods is known for the isolation or synthesis of astaxanthin. Thus, for example, the isolation of astaxanthin by extraction from crustacean shells is disclosed in WO-A 86/6082. Furthermore, astaxanthin can be obtained by fermentation processes (cf. Biotechnol. Letters 10 (1988) 609–614) or from micro-algae (cf. WO-A 89/1977 and EP 329 754). However, these methods have crucial disadvantages. On the one hand, astaxanthin is present in nature only in very low concentration and must therefore be isolated by elaborate processes. On the other hand, only unsatisfactory yields are obtained. In addition, the large amounts of auxiliaries required and waste materials which are produced and cannot be utilized are ecologically and economically unacceptable.

Of the processes for the synthetic preparation of astaxanthin, mention may be made of the oxidation of canthaxanthin bis-silyl enol ethers with percarboxylic acids and subsequent hydrolysis (cf. EP 101 597). The disadvantages of this process are the only moderate yields and purities of astaxanthin, incomplete conversions and unwanted byproducts such as adonirubin.

EP 440 037 discloses another method for the oxidation of canthaxanthin enolates. However, this process is also unsuitable for industrial preparation because costly bases, such as the salts of hexamethyldisilazane, and very low temperatures are needed to prepare the enolates, and the oxidizing agent used is phenylsulfonyloxaziridine which is difficult to obtain and troublesome from the point of view of safety. Moreover, only incomplete conversion is obtained in this process too.

EP 05 749 discloses a process for the preparation of astaxanthin by Wittig reaction of a building block which is acylated on the hydroxyl group in position 4 of the asta-$C_{15}$-triarylphosphonium salt with $C_{10}$-dial, followed by hydrolysis. The solvent mentioned for this Wittig reaction is, inter alia, isopropanol. The disadvantages of this process are that protective groups must be introduced into the $C_{15}$-triphenylphosphonium salts and eliminated again, and the yields obtained are moderate.

EP 057 48A2 describes the Wittig reaction of asta-$C_{15}$-triarylphosphonium salts themselves with $C_{10}$-dial. Solvents mentioned as suitable are halohydrocarbons such as methylene chloride and chloroform. The disadvantage of this process is that large amounts of halohydrocarbons are required both as solvents and for the workup by extraction, and these are known to have objectionable toxicological properties and require technically elaborate recovery.

Furthermore, several publications in Helv. Chim. Acta 64 (1981; cf. pages 2405–18; 2436–46 and 2447–62) describe the Wittig reaction of asta-$C_{15}$-triarylphosphonium halides with the $C_{10}$-dial. In all the Wittig reactions described, methylene chloride is used as solvent for the phosphonium salts and the $C_{10}$-dialdehyde, and methylene chloride is used for the workup and purification. The disadvantages of this are that methylene chloride requires, as a very volatile toxicologically objectionable halohydrocarbon, very elaborate apparatus in an industrial process and, in addition, methylene chloride may form adducts with astaxanthin, which would result in chlorine-containing products.

It is an object of the present invention to improve the process for the preparation of astaxanthin from an asta-$C_{15}$-triarylphosphonium salt and the $C_{10}$-dialdehyde in a Wittig reaction so that the reaction can be carried out in an industrially straightforward manner without using chlorinated hydrocarbons and without using solvent mixtures which are difficult to work up.

We have found that this object is achieved by preparing astaxanthin in an industrially straightforward manner and in very good yields by using only methanol, ethanol or methanol and ethanol mixed with water both for the Wittig reaction and for the workup.

Although carotenoid syntheses in pure alkanol have been disclosed in the literature (cf. DE 1 068 703 and DE 954 247), β-ionyl-ideneethyltriphenylphosphonium salts were used to synthesize β-carotene therein. The differences in solubility and polarity of the precursors and products are considerable when the unsubstituted β-carotene is compared with the highly substituted astaxanthin and thus no conclusion can be drawn by analogy. The alphahydroxy keto group in astaxanthin is much more reactive than pure polyenes and is capable of a large number of side reactions in basic and acidic medium, such as the formation of semiastacin, astacin and diosphenols (cf. Helv. Chim. Acta 64 (1981), 2436–46 and O. Isler, Carotenoids, Birkhäuser-Verlag (1971), pages 140 and 141).

Although DE 2 653 838 also mentions alkanols in the synthesis of 15,15'-dehydroastaxanthin, the only one expressly mentioned, besides dichloromethane and dimethylformamide, is isopropanol. Moreover, the required product is additionally extracted with methylene chloride and recrystallized from chloroform/methanol or pyridine/water. This shows that it was regarded as impossible to obtain the product efficiently without using, in particular, chlorinated hydrocarbons for astaxanthin derivatives.

In addition, when isopropanol or isobutanol is used as solvent for the Wittig reaction, only unsatisfactory yields of astaxanthin are obtained (see also Comparative Examples 7 and 8). It was all the more astonishing to find that astaxanthin or astaxanthin derivatives can be prepared very advantageously, in high yield and selectivity, in pure methanol or ethanol or mixtures of methanol or ethanol with water.

The invention therefore relates to a process for the preparation of astaxanthin of the formula I

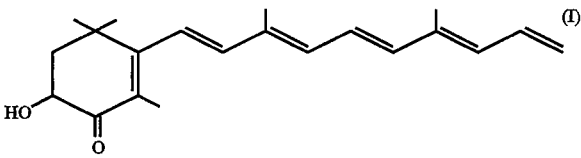

by reaction of 2 mol of the triphenylphosphonium salt of the general formula II

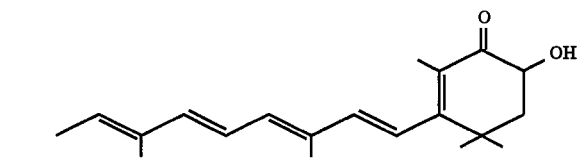

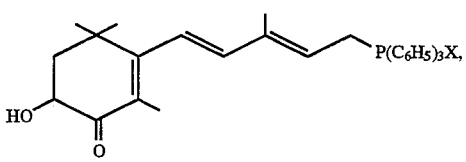

where X is chlorine, bromine or $HSO_4—$, preferably bromine, in a Wittig reaction with one mol of the $C_{10}$-dialdehyde of the formula III

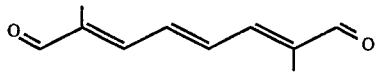

wherein

- A. the starting compounds of the formulae II and III are suspended in methanol, ethanol or a mixture of methanol or ethanol with water, and the suspension is heated to from 30° to 80° C., preferably 40° to 60° C., until a homogeneous solution has formed,
- B. from 1 to 1.2, preferably 1 to 1.1, mol of a base are added per mol of triphenylphosphonium salt to the resulting homogeneous solution at from 20° to 40° C., and
- C. after the reaction is complete, where appropriate, the amount of water necessary to precipitate the astaxanthin is added to the reaction mixture.

The astaxanthin obtained according to the invention is generally converted into the all-(E)-isomer by thermal isomerization.

The thermal isomerization, or the isomerization and purification, generally takes place satisfactorily by heating in a $C_1-C_4$-alkanol, in hexane, heptane, water or mixtures of these solvents to from 60° to 120° C., preferably 80° to 100° C., under reflux or in a closed vessel.

The process is particularly advantageous when the resulting astaxanthin is isomerized by heating in methanol or ethanol to from 60° to 120° C., preferably 80° to 100° C., in a closed vessel.

The amount of methanol or ethanol generally used in the reaction according to the invention is such that the concentration of the triphenylphosphonium halides in the alkanol is from 0.1 to 3 mol, preferably 0.3 to 1 mol, per liter of alkanol.

The general procedure for completely dissolving the precursors of the formulae II and III is to introduce them in any sequence into the alkanol and to heat the suspension to from 30° to 40° C., preferably 50° to 60° C. The water content in the reaction mixture is advantageously from 0 to 25% by weight in these cases.

The base is slowly introduced into the resulting solution, generally at from 0° to 80° C., preferably 10° to 30° C.

Bases which may be mentioned as suitable for Wittig reactions are: solutions of alkali metal or alkaline earth metal alkoxides or alkali metal or alkaline earth metal hydroxides in methanol or ethanol, alkali metal or alkaline earth metal hydroxides, ammonia, triethylamine, and alkali metal or alkaline earth metal carbonates. The process is particularly advantageous when an aqueous solution of NaOH or KOH, a methanolic sodium methoxide solution or an ethanolic sodium ethoxide solution is used.

The times taken to dissolve the precursors and introduce the bases and for the reaction are generally from 0.5 to 12 hours, preferably 1 to 8 hours.

The reaction mixture is worked up by adding water unless it already contains the amount of water necessary to precipitate the astaxanthin.

It is advantageous for the isolation if the reaction mixture contains about 0.1–10, preferably 0.5–2, parts by volume of water per part by volume of alkanol.

It is particularly advantageous to carry out the isolation of the astaxanthin at from 40° to 80° C., preferably 50° to 60° C.

The crystallized astaxanthin is isolated by filtration or centrifugation and washed with methanol, ethanol and/or mixtures of these alkanols with water.

To convert the resulting mixture of E/Z isomers into the all-(E)-astaxanthin which is in particular demand it is generally subjected to a thermal treatment. The thermal isomerization of the astaxanthin obtained according to the invention is advantageously carried out in such a way that the crystals which are still moist with water, alkanol or water/alkanol are suspended in a $C_1-C_4$-alkanol, preferably methanol or ethanol, in heptane, water or mixtures of these solvents and heated to from 60° to 120° C., preferably 70° to 100° C., either under reflux under atmospheric pressure or in a closed vessel under the pressure set up therein.

The process according to the invention is particularly advantageous when the astaxanthin-containing reaction mixture is neutralized with acetic acid before the thermal isomerization because the oxygen functionalities in the astaxanthin ring are more sensitive in alkaline medium.

The isomerization times depend on the temperature and are from 0.5 to 16 hours, in particular 1 to 10 hours.

The process according to the invention can be used to obtain astaxanthin, which is in demand as food colorant, in yields of up to 88% of theory and with selectivities in respect of the all-(E) configuration of up to 99%.

EXAMPLES 1 TO 8

(Examples 7 and 8 are comparative examples)

In each case, 132.5 g (0.228 mol) of 3-methyl-5-(2,6,6-tri-methyl-3-oxo-4-hydroxy-1-cyclohexenyl)-2,4-pentadienyltriphenylphosphonium bromide (asta-$C_{15}$-triphenylphosphonium bromide) and 16.6 g (0.1 mol) of 2,7-dimethyl-2,4,6-octatrienedial (99% by weight; all-E/4Z=2/1) were suspended at 25° C. in 500 ml of the alkanol specified in the following table. The mixture was heated to the temperature evident from the table, resulting in a homogeneous solution. After brief stirring at 50° C., the solution was cooled to about 25° C. and the base which is evident from the table was added at the temperature which is evident from the table over the time which is evident from the table.

The mixture was then stirred at the temperature which is evident from the table for 2 hours (h). For workup, the amount of water which is evident from the table was added to the reaction mixture at 25° C., the mixture was then stirred at the temperature which is evident from the table for the time which is evident from the table and subsequently the suspension of astaxanthin crystals was filtered with suction, washing with a 60% by volume alkanol/water mixture and with warm water.

For the isomerization, the crystals moist with water were dissolved in 200 ml of the alkanol evident from the table and refluxed for several hours (Examples 1, 3 and 5) or heated at 95°–100° C. in a pressure vessel (Examples 2, 4 or 6). The mixture was then cooled to 25° C., and the crystals were filtered off with suction and washed with the appropriate alkanol. The astaxanthin crystals were dried to constant weight at 50° C. and 1 mbar.

The yields of astaxanthin have been indicated in the table in g and in % of theory based on $C_{10}$-dialdehyde. The all-E content and the melting point m.p. of the astaxanthin obtained in each case are also indicated in the table.

Examples 7 and 8 using isopropanol and isobutanol, respectively, are only comparative examples.

TABLE

| Example | Alkanol | Heating to [°C.] | Base addition Time [h] | Base addition Temp. [°C.] | Base addition Type Amount (mol) | Subsequent stirring at [°C.] | Water [ml] | Subsequent stirring Time [h] | Subsequent stirring Temp. [°C.] | Alkanol for isomer. | all-E Yield [g(%)] | all-E content [%] | M.p. [°C.] |
|---|---|---|---|---|---|---|---|---|---|---|---|---|---|
| 1 | Methanol | 50 | 1 | 25–30 | 30% strength NaOCH$_3$) (0.228) | 25 | 330 | 2 | 60 | Ethanol | 52.7 (88:4) | 97.7 | 210 |
| 2 | Methanol | 50 | 1 | 25–30 | 30% strength NaOCH$_3$ (0.228) | 25 | 330 | 2 | 60 | Methanol | 50.9 (85.5) | 97.9 | 209 |
| 3 | Ethanol | 50 | 1 | 25–30 | 50% strength NaOH (0.228) | 25 | 300 | 2 | 60 | Ethanol | 50.7 (85) | 97.7 | 209 |
| 4 | Ethanol | 50 | 1 | 25–30 | 20% strength NaOC$_2$H$_5$ (0.228) | 25 | 300 | 2 | 60 | Ethanol | 51.8 (86.8) | 99.1 | 208 |
| 5 | Ethanol | 50 | 2 | 25–55 | 10% strength Na$_2$CO$_3$ in water (0.24) | 55 | — | 2 | — | Ethanol | 43 (72) | 98 | 210 |
| 6 | Methanol | 50 | 1 | 25–30 | 10% strength Na$_2$CO$_3$ in water (0.24) | 55 | — | 2 | 55 | Methanol | 40 (67) | 97.1 | 209 |
| 7* | Isopropanol | 80 | 1 | 80 | 30% strength NaOCH$_3$ (0.228) | 80 | 330 | 2 | 80 | — | 31.8 (53.3) | 96 | 212 |
| 8* | Isobutanol | 40 | 1 | 40 | 30% strength NaOCH$_3$ (0.228) | 25 | 330 | 2 | 80 | — | 30.4 (51) | 96.5 | 210 |

*= Comparative examples (without additional isomerization)

EXAMPLE 9

132.5 g (0.228 mol) of asta-C$_{15}$-triphenylphosphonium chloride (99% pure) and 16.6 g (0.1 mol) of C$_{10}$-dialdehyde (99% pure; all-E/4Z=2/1) were suspended in 500 ml of ethanol at 25° C. The mixture was heated to 50° C., resulting in a homogeneous solution. After briefly stirring at 50° C., it was cooled to 25° C. and 50% strength aqueous NaOH (18.3 g=0.228 mol) was added as base at 25°–30° C. over the course of 1 h. The mixture was subsequently stirred at 25° C. for 2 h. For workup, 300 ml of water were added at 25° C. The mixture was heated to 60° C. and stirred at this temperature. The suspension of astaxanthin crystals was then filtered with suction, washing with a 60% by volume ethanol/water mixture and with warm water.

For the isomerization, the E/Z-astaxanthin crystals moist with water were suspended in 200 ml of ethanol and refluxed for several h. The mixture was cooled to 25° C., and the crystals were filtered off with suction and washed with ethanol. They were dried to constant weight at 50° C./1 mbar.

Yield: 46.8 g of astaxanthin (corresponding to 78.5% based on C$_{10}$-dialdehyde); the all-E content by HPLC was 97.1%; m.p. 211° C.

EXAMPLE 10

132.5 g (0.228 mol) of asta-C$_{15}$-triphenylphosphonium chloride (99% pure) and 16.6 g (0.1 mol) of C$_{10}$-dialdehyde (99% pure; all-E/4Z=2/1) were suspended in 500 ml of ethanol at 25° C. The mixture was heated to 50° C., resulting in a homogeneous solution. After briefly stirring at 50° C., it was cooled to 25° C. and a 20% strength solution of NaOEt (77.6 g=0.228 mol) in ethanol was added as base at 25°–30° C. over the course of 1 h. The mixture was subsequently stirred at 25° C. for 2 h. For workup, 300 ml of water were added at 25° C. The mixture was heated to 60° C. and stirred at this temperature. The suspension of astaxanthin crystals was then filtered with suction, washing with a 60% by volume ethanol/water mixture and with warm water.

For the isomerization, the E/Z-astaxanthin crystals moist with water were suspended in 200 ml of ethanol and heated at 100° C. in a closed vessel under the autogenous pressure of about 1.5 bar for several h. The mixture was cooled to 25° C., and the crystals were filtered off with suction and washed with ethanol. They were dried to constant weight at 50° C./1 mbar.

Yield: 50.7 g of astaxanthin (corresponding to 85% based on the C$_{10}$-dialdehyde); the all-E content by HPLC was 97%; m.p. 211°–213° C.

EXAMPLE 11

132.5 g (0.228 mol) of asta-C$_{15}$-triphenylphosphonium chloride (99% pure) and 16.6 g (0.1 mol) of C$_{10}$-dialdehyde (99% pure; all E/4-Z=2/1) were suspended in 500 ml of ethanol at 25° C. The mixture was heated to 50° C., resulting in a homogeneous solution. After briefly stirring at 50° C., it was cooled to 25° C. and a 20% strength solution of NaOEt (77.6 g=0.228 mol) in ethanol was added as base at 25°–30° C. over the course of 1 h. The mixture was subsequently stirred at 25° C. for 2 h. 3.06 g (0.051 mol) of glacial acetic acid were then added to the reaction mixture. For workup, 300 ml of water were added at 25° C. The mixture was heated to 60° C. and stirred at this temperature. The suspension of astaxanthin crystals was then filtered with suction, washing with a 60% by volume ethanol/water mixture and with warm water.

For the isomerization, the E/Z astaxanthin crystals moist with water were suspended in 200 ml of ethanol and heated at 100° C. under the autogenous pressure of about 1.5 bar for 16 h. The mixture was cooled to 25° C and the crystals were filtered off with suction and washed with ethanol. They were dried to constant weight at 50° C./1 mbar.

Yield: 52.8 g (88.5% based on $C_{10}$-dialdehyde); the all-E content by HPLC was 96%; m.p. 212°–214° C.

We claim:

1. A process for the preparation of astaxanthin of the formula I

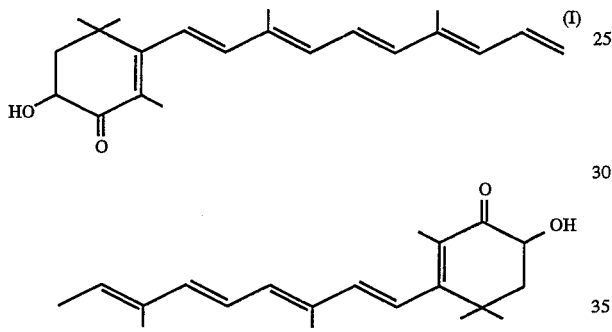

by reaction of 2 mol of the triphenylphosphonium salt of the general formula II

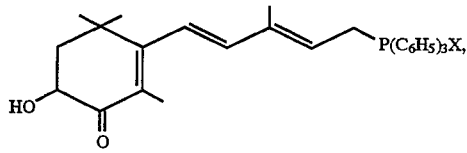

where X is chlorine, bromine or $HSO_4$—, in a Wittig reaction with one mol of the $C_{10}$-dialdehyde of the formula III

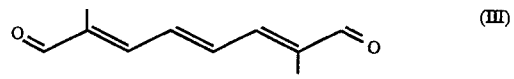

wherein

A. the starting compounds of the formulae II and III are suspended in methanol, ethanol or a mixture of methanol or ethanol with water, and the suspension is heated to from 30° to 80° C. until a homogeneous solution has formed, B. about 1 mol of a base which is conventional for Wittig reactions is added per mol of triphenylphosphonium salt to the resulting homogeneous solution at from 20° to 40° C., and C. after the reaction is complete, where appropriate, the amount of water necessary to precipitate the astaxanthin is added to the reaction mixture, and the crystallized astaxanthin is isolated.

2. A process as claimed in claim 1, wherein a triphenylphosphonium salt of the general formula II where X is bromine is reacted with the $C_{10}$-dialdehyde of the formula III.

3. A process as claimed in claim 1, wherein in step B an aqueous solution of sodium hydroxide or potassium hydroxide, a methanolic sodium methoxide solution or an ethanolic sodium ethoxide solution is added to the homogeneous solution of the starting compounds.

4. A process as claimed in claim 1, wherein the resulting astaxanthin is isomerized, or isomerized and purified, by heating in a $C_1$–$C_4$-alkanol, in heptane, water or mixtures of one or more of these solvents to from 60° to 120° C. under reflux under atmospheric pressure or in a closed vessel.

5. A process as claimed in claim 1, wherein the resulting astaxanthin is isomerized, or isomerized and purified, by heating in methanol or ethanol to from 80° to 100° C. in a closed vessel under the autogenous pressure of the solvent.

* * * * *